United States Patent

Heinonen et al.

[11] Patent Number: 5,490,499
[45] Date of Patent: Feb. 13, 1996

[54] REGULATION OF A PROPELLANT GAS FLOW

[75] Inventors: Erkki Heinonen; Markku Hyvönen, both of Helsinki, Finland

[73] Assignee: Instrumentarium Corp., Finland

[21] Appl. No.: 19,464

[22] Filed: Feb. 18, 1993

[30] Foreign Application Priority Data

Feb. 21, 1992 [FI] Finland .................................. 920779

[51] Int. Cl.⁶ .............................................. A61M 16/00
[52] U.S. Cl. .................. 128/203.28; 128/204.21; 128/205.15
[58] Field of Search .................. 128/203.28, 204.18, 128/204.21, 205.13, 205.15, 204.28, 205.17, 205.14, 205.18

[56] References Cited

U.S. PATENT DOCUMENTS

| | | | |
|---|---|---|---|
| 3,556,095 | 1/1971 | Ismach | 128/204.28 |
| 4,256,100 | 3/1981 | Levy et al. | 128/204.21 |
| 4,340,044 | 7/1982 | Levy et al. | 128/204.21 |
| 4,637,385 | 1/1987 | Rusz | 128/204.21 |
| 4,702,240 | 10/1987 | Chaoui | 128/204.18 |
| 4,883,051 | 11/1989 | Westenskow et al. | 128/204.21 |
| 4,932,401 | 6/1990 | Perkins | 128/203.12 |

FOREIGN PATENT DOCUMENTS

| | | |
|---|---|---|
| 93503 | 3/1983 | European Pat. Off. . |
| 347015 | 7/1985 | European Pat. Off. . |
| 166305 | 10/1987 | European Pat. Off. . |
| 282675 | 9/1988 | European Pat. Off. . |
| 504977 | 9/1992 | European Pat. Off. . |
| 2813270 | 10/1979 | Germany . |
| 418456 | 6/1981 | Sweden . |
| 1175714 | 12/1969 | United Kingdom . |
| 80-01646 | 8/1980 | WIPO . |

*Primary Examiner*—Edgar S. Burr
*Assistant Examiner*—Eric P. Raciti
*Attorney, Agent, or Firm*—Andrus, Sceales, Starke & Sawall

[57] ABSTRACT

An apparatus for the regulation of a gas volume delivered to a patient during a respiratory cycle. The apparatus includes at least one valve (9 or 8) for discharging some of the propellant gas flowing from a propellant gas source (4) into a propellant gas chamber (18), the propellant gas chamber (18) being at least partially defined by a wall (17), having a second chamber (19) on the other side thereof. The location of said wall changes as the propellant gas pressure increases in the propellant gas chamber, thus increasing the volume of the propellant gas chamber, the volume of second chamber (19) on the other side of wall (17) diminishing, thus forcing the gas being delivered to a patient to flow towards a patient (21). Thereafter, in order to perform the exhalation of a patient, the propellant gas chamber pressure is allowed to discharge through a valve (9 or 8), whereby the volume of propellant gas chamber (18) diminishes and the volume of second chamber (19) increases as a result of the displacement of the wall (17). Between the propellant gas chamber (18) and propellant gas source (4) is a pressure regulating element (6), capable of regulating the pressure of the propellant gas flowing from the propellant gas source. A method for the regulation of a propellant gas flow to be delivered into a propellant gas chamber (18) and supplied from a propellant gas source (4) by pressure regulation of the propellant gas.

18 Claims, 3 Drawing Sheets

5,490,499

REGULATION OF A PROPELLANT GAS FLOW

BACKGROUND OF THE INVENTION

1. Field of the Invention

The present invention relates to an apparatus for the regulation of a gas volume delivered to a patient during a respiratory cycle, said apparatus comprising at least one valve for discharging some of the propellant gas which flows from a propellant gas source into a propellant gas chamber, and said propellant gas chamber being at least partially defined by a wall with a second chamber on the other side thereof and the location of said wall changing as the pressure of propellant gas increases in the propellant gas chamber to increase the volume of said propellant gas chamber, whereby the volume of said second chamber on the other side of the wall diminishes, forcing the gas to be delivered to a patient to flow towards a patient whereafter, in order to perform the exhalation of patient through the valve, the pressure of said propellant gas chamber is allowed to discharge for diminishing the volume of the propellant gas chamber and increasing the volume of the second chamber as a result of the wall displacement. The invention relates also to a method for regulating a gas volume.

A ventilator is a respiratory device for carrying out the ventilation of a patient's lungs when the patient's own respiratory action is insufficient or completely stopped.

The structure of ventilators using a pressurized gas as the propelling force can be divided in three components: a control unit, a bellows unit, and a patient circuit. An object of the control unit is to carry out control parameters characterizing the pulmonary ventilation; such as tidal volume, respiration frequency, the ratio of inhalation and exhalation times as well as an inhalation pause. The bellows unit separates patient circuit unit and the patient loop of a ventilator using a pressurized gas as the propelling force. An object of the bellows unit is to prevent the respiratory gases of a patient and the propellant gas from mixing with each other. An object of the patient circuit is to provide separate passages for inhalation and exhalation gases to and from a patient as well as to remove carbon dioxide from exhalation gases.

2. Description of the Related Art

Traditionally, in ventilators using a pressurized gas as the propelling force, a tidal volume to be delivered into a patient's tube system is determined by means of a propellant gas flow and its duration. In U.S. Pat. No. 4,637,385, a propellant gas flow is regulated by throttling a gas source with a needle valve. The position of the needle valve can be controlled by means of a microprocessor and a motor. The position of the needle valve is indicated by a mechanical signal which is converted into an electric signal. Drawbacks of this solution include sensitivity to calibration errors and needle valve malfunctions.

EP Patent publication No. 282,675 describes a flow control valve intended for a ventilator, to which is delivered a stabilized propelling pressure from a gas source. A patient's respiratory gases are carried through said valve under the control of a stepping motor and a microprocessor. The flow control valve is regulated by a stepping motor with predetermined control data for delivering a tidal volume to a patient. Said valve is opened to match a required inhalation flow and it is kept open for the duration of a tidal volume delivery. A microprocessor is used to compensate for the effect that the flows occurring at the time of opening and closing the valve have on the tidal volume. The control valve operates on an open-loop principle, which is characterized by inaccurate control. The compensation of an opening and closing time requires a high peak flow. If this is to be minimized by using a high-speed valve, the accuracy of ventilation will be impaired even further.

U.S. Pat. No. 4,256,100 discloses an anaesthesia ventilator, wherein a propellant gas flow is controlled by five binary weighted valves. A regulated propellant gas pressure is delivered according to a predetermined flow through one of the valves into a collecting chamber and further to a bellows unit. The maximum temporary flow is achieved when all valves are simultaneously open. A tidal volume is determined in relation to preset respiration frequency, inhalation and exhalation times as well as by means of a flow rate per minute by using a microprocessor. A problem in the cited invention is that the realization of a large dynamic area together with resolution requires a plurality of valves. For example, a peak flow of 100 1/min. and a resolution of 0.1 1/min. require ten valves and, thus, the solution will be expensive, complicated, bulky and demands a lot of power.

SUMMARY OF THE PRESENT INVENTION

An object of the present invention is to eliminate the above problems. An object is to provide a method and an apparatus for regulating a propellant gas flow to be delivered into a bellows unit included in a ventilator so as to match the respiratory needs of a patient. Another object is to provide a reliably operating and simple method and apparatus for regulating as accurately as possible a propellant gas flow to be delivered into a bellows unit included in a ventilator.

The characterizing features of the invention are set forth in the appended claims.

In a solution of the invention, the regulation of a propellant gas for a ventilator is based on the application of a varying propelling pressure in controlling a gas volume to be delivered to a patient during an inhalation period. The regulation of a varying propelling pressure is effected by means of a pressure regulating element. Such an element is often referred to as a pressure regulator relief valve.

A typical propellant gas source is a hospital's pressurized gas supply system, pressure cylinders or a compressor. Typical supply pressures vary within the range of 2.7–8 bars. The initial pressure of a pressure regulating element is adjusted to match a desired propellant gas flow.

Thus, the pressure of a gas flowing from a propellant gas source is varied by means of a pressure regulating element before the flow reaches a propellant gas chamber, which is included in a bellows unit and whose operation determines the volume of a gas delivered into the lungs of a patient. The amount of gas contained in the single inhalation of a patient is usually referred to as the tidal volume. The pressure of a propellant gas, together with the flow resistance of a gas duct, has an effect on the gas flow rate, which in turn has an effect on how rapidly the volume of said propellant gas chamber increases. The rate is set so as to attain a desired tidal volume within a certain time frame. As the volume of the propellant gas chamber increases, the volume of another chamber, included in a patient circuit and located on the other side of the wall of the propellant gas chamber, decreases accordingly as the gas from the chamber flows into the lungs of a patient. In order to avoid pressure-induced lung damage, it is essential that a tidal volume be generated with an intra-pulmonary pressure which is as low as possible. In order to minimize the pressure, the peak flow should preferably be as low as possible. The peak flow is lower, the longer a time used for inspiration. In order to maximize the time, the flow should have a rise and fall time which is as short as possible.

Preferably, the propellant gas flow is adjusted linearly by varying the propelling pressure over a constant throttle, i.e. an effort is made to distribute the propellant gas flow uniformly throughout the entire inhalation cycle.

Thus, a conventional bellows unit comprises a propellant gas chamber, which is at least partially defined by a wall whose location changes as a result of pressure and the volume of a chamber located on the other side of said wall in turn undergoes a change in the reversed direction relative to the volume of said propellant gas chamber. One example of a wall relocating its position as a result of pressure is e.g. a bellows or a bag. A propellant gas chamber is often located outside such bellows or bag and inside it lies a patient loop chamber whereby, as the pressure in the propellant gas side increases, the bellows or bag will be compressed.

During the exhalation of a patient, the pressure prevailing in a patient circuit is allowed to fall. This is preferably effected in a manner that the pressure of a propellant gas bearing effect on the bellows in the side of a control unit is allowed to drop at least to such a degree that the gas contained in the lungs of a patient can escape out.

The inhalation and exhalation cycle requires that between a propellant gas source and a bellows unit on the propellant gas side be preferably located a valve, which can be opened and closed whenever necessary. More preferably, the valve is located between a pressure regulating element and a bellows unit. This valve is herein referred to as an inspiration valve. Thus, by means of this valve it is possible to control the operation of the bellows. When the valve is open, the gas is able to flow into the bellows unit and, thus, the bellows will be compressed. When the bellows is sufficiently compressed, the valve is closed and, thus, pressure applied on the bellows from the direction of the propellant gas chamber can no longer increase.

The inspiration valve is preferably a high-speed on/off-valve which facilitates a short rise and fall time for the flow, said time being preferably less than 40 ms. An inspiration valve is required whenever the rise and fall speed of a pressure regulating valve is not sufficient. If the rise and fall speed of a pressure regulating valve is sufficiently high, preferably less than 50 ms, the inspiration valve can be omitted. Such a pressure regulating valve can be e.g. voltage-controlled.

In order to facilitate the exhalation of a patient, the pressure of a propellant gas chamber is reduced. This is effected by way of a valve. This outlet valve is preferably spaced apart from an inspiration valve but the inspiration valve itself may possess a function, whereby the pressure can be discharged from the propellant gas chamber. The outlet valve is also often referred to as an expiration valve. Preferably, the outlet valve reduces the pressure prevailing between the bellows and the inspiration valve. While the pressure between the valve and the bellows is falling, the bellows strives to reform since the pressure from the other side of the bellows, i.e. from the direction of a patient circuit rises to exceed the former pressure.

In order to facilitate the inhalation of a patient, the outlet valve is closed and an inspiration valve located between a gas source and a bellows unit will be opened. This cycle is repeated as long as necessary.

A solution of the invention does not require a separate flow control valve, such as a needle valve, for the regulation of a propellant gas flow. The solution is capable of reducing the number of easily damaged components as well as the price of the apparatus. Preferably, the regulation of a propellant gas flow can also include a feedback for an improved regulation reliability and tidal volume accuracy. The feedback provides an improved possibility of monitoring the changes occurring in a gas space located between a pressure regulating element and a bellows unit and, on the basis of thus obtained information, the adjustment of a pressure regulating element can be effected to correspond more closely to desired values. A simple feedback can be based e.g. on the visual observation of the position of a bellows. However, the feedback is more preferably effected by means of flow measurement and/or pressure measurement for a safe operation of the apparatus. The solution is also simple in design.

BRIEF DESCRIPTION OF THE DRAWING

The invention will now be described in more detail with reference made to the accompanying drawings, in which.

DESCRIPTION OF THE PREFERRED EMBODIMENTS

Figure 1:
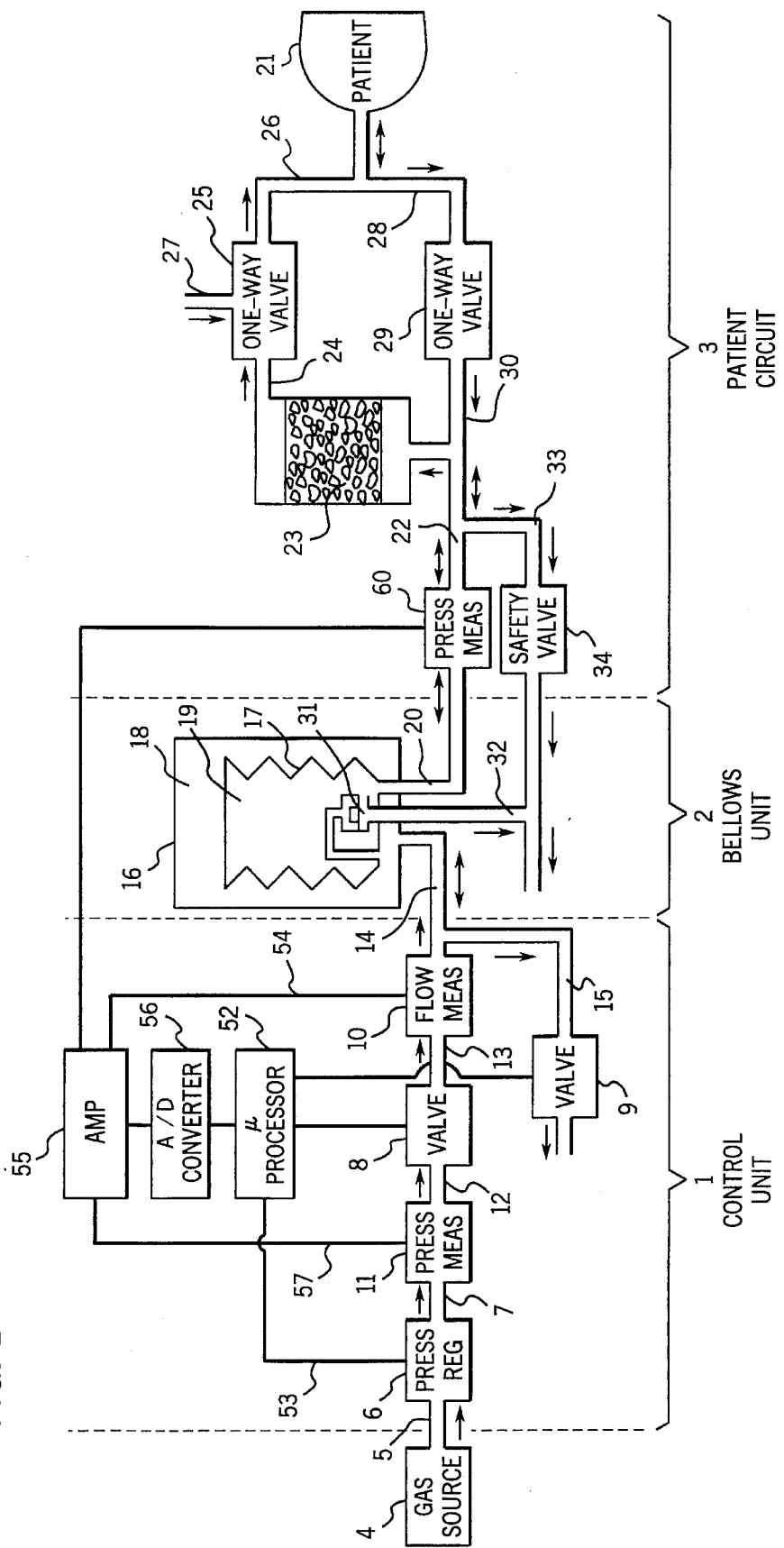
FIG. 1 shows a schematic view of a ventilator system, illustrating an apparatus of the invention, which apparatus can be used for the application of a method of the invention.

FIG. 1 shows a preferred ventilator system roughly divided in three sections, i.e. a control unit 1, a bellows unit 2, and a patient circuit 3. The control unit, wherein the gas coming from a propellant gas source 4 is delivered along a duct 5, is provided with a pressure regulating element 6 for regulating the pressure of a propellant gas flow being delivered into bellows unit 2 so as to attain a desired propellant gas flow between element 6 and the bellows unit. The pressure reduction of a propellant gas flowing from propellant gas source 4 effected by means of pressure regulating element 6 decreases the propellant gas flow proceeding from element 6 along a duct 7 as compared to the situation prevailing in duct 5. Furthermore, for opening and closing a gas communication between propellant gas source 4 and bellows unit 2, the control unit is preferably provided with a valve 8, preferably a magnetic valve. Valve 8 is here referred to as an inspiration valve. The reduction of a propellant gas pressure generated in bellows unit 2 requires a valve 9, which is here referred to as an outlet valve and which is preferably a magnetic valve. Instead of two separate valves 8 and 9, there could be just a single valve 8 or 9, which would carry out the functions of both the inspiration and outlet valve. When the outlet valve is closed, the propellant gas pressure in the bellows unit increases if the inspiration valve is open.

Between pressure regulating element 6 and bellows unit 2 is preferably coupled a flow measuring element 10 for the determination of a propellant gas flow, said element being preferably a pressure-difference measuring element. The flow measuring element could also be located between propellant gas source (4) and the pressure regulating element. The measurement of a propellant gas flow can also be effected in some other way. The most preferred embodiment is a solution, wherein the prevailing pressure is also measured between pressure regulating element 6 and the bellows unit. Therefore, said duct 7 extending from element 6 is fitted with a pressure measuring element 11, which preferably compares the pressure downstream of element 6 with the pressure of ambient air. Such conventional pressure measuring elements are commercially available in abundance.

In a preferred solution illustrated in FIG. 1, said pressure measuring element 11 is connected by way of a duct 12 to valve 8, which in turn is further connected by way of a duct 13 to flow measuring element 10. To a duct 14 extending from the flow measuring element to the bellows unit is attached a duct 15, provided with an outlet valve 9. This sequence is preferred but not absolutely necessary in view of the control unit operation.

The bellows unit 2, whose operation is primarily controlled by means of a propellant gas flow under the control of a control unit, and the patient circuit 3 are as such conventional and prior known technology. The bellows unit comprises generally a housing 16, which encloses a propellant gas chamber 18 at least partially defined by a wall 17, whose position changes as a result of the gas pressure. This mobile wall 17 is preferably a bellows or a bag, whereby its condition is easily reformed after a pressure variation.

Thus, from the control unit said propellant gas flows along duct 14 into propellant gas chamber 18 located between housing 16 and wall 17. When the propellant gas pressure in chamber 18 exceeds the pressure prevailing on the other side of the wall, in this case in another chamber 19 located inside the bellows, the bellows strives to compress since the volume of propellant gas chamber 18 increases as that of chamber 19 decreases. The compression continues for as long as inspiration valve 8 is open and said outlet valve 9 for discharging the propellant gas from the control unit is closed. The inspiration valve is closed for bringing the exhalation period of a patient to an end.

The gas contained in chamber 19 located inside the bellows flows along a duct 20 towards the lungs of a patient 21 as the bellows is compressing. The pressure of a gas flowing in duct 20 can possibly be measured by means of a pressure measuring element 60. This is followed by delivering the gas along a duct 22 to a conventional carbon dioxide absorber 23 and therefrom further along a duct 24 to a valve 25, which is preferably a one-way valve only allowing a gas flow towards a patient. From the one-way valve extends a duct 26 to the respiratory tracts of a patient 21. The gas having travelled through carbon dioxide absorber 23 can be supplemented by delivering along a duct 27 some fresh gas, which usually contains oxygen and nitrous oxide and often also some anaesthetic.

A single volume to be delivered to a patient is dependent on a fresh gas flow to be supplied to a patient circuit as well as on the compliance of the ducts included in a ventilator and a patient circuit. The effect of a fresh gas flow on the tidal volume to be delivered to a patient can be preferably compensated by subtracting from a desired tidal volume the volume of a fresh gas flowing during the course of inspiration. The compliance of the ducts included in a ventilator and a patient circuit can be preferably measured at the ventilator preparation stage by delivering a propellant gas to the patient circuit and by measuring the pressure increase in the patient circuit by means of pressure measuring element 60 and the volume delivered to the patient circuit by means of flow measuring element 10.

At the commencement of an exhalation cycle said inspiration valve 8 is closed and outlet valve 9 is opened for allowing the positive pressure prevailing in chamber 18 to discharge preferably to the level of ambient air pressure. During the exhalation of a patient the exhalation gas flows along a duct 28 to a valve 29, which is also preferably a one-way valve preventing a reversed gas flow, and therefrom further along a duct 30, 22 and 20 into chamber 19 inside bellows 17 striving to raise the bellows towards its original condition or, in the case of FIG. 1, towards the top section of housing 16 as a result of the positive pressure level prevailing in the lungs of patient and in the patient circuit. Thus, it is necessary that the pressure prevailing in propellant gas chamber 18 between housing 16 and bellows 17 has fallen below the positive pressure level prevailing in the patient circuit. When the pressure level inside bellows 17 is sufficiently high, which in the case of FIG. 1 takes place as the bellows comes into contact with the top section of housing 16, a valve 31, which can be e.g. a pop-off valve, will be opened for allowing the extra patient gases to escape along a duct 32 out of the patient circuit. To be on the safe side, a duct 33 is used to connect duct 22 to a safety valve 34 for automatically discharging the excess pressure accumulated in the patient circuit.

After the exhalation cycle said outlet valve 9 is closed and inspiration valve 8 is re-opened for commencing the inhalation of a patient. The respiration cycles are successively repeated within this sequence of events. The fresh gas flow along duct 27 continues generally throughout the process.

Figure 2:
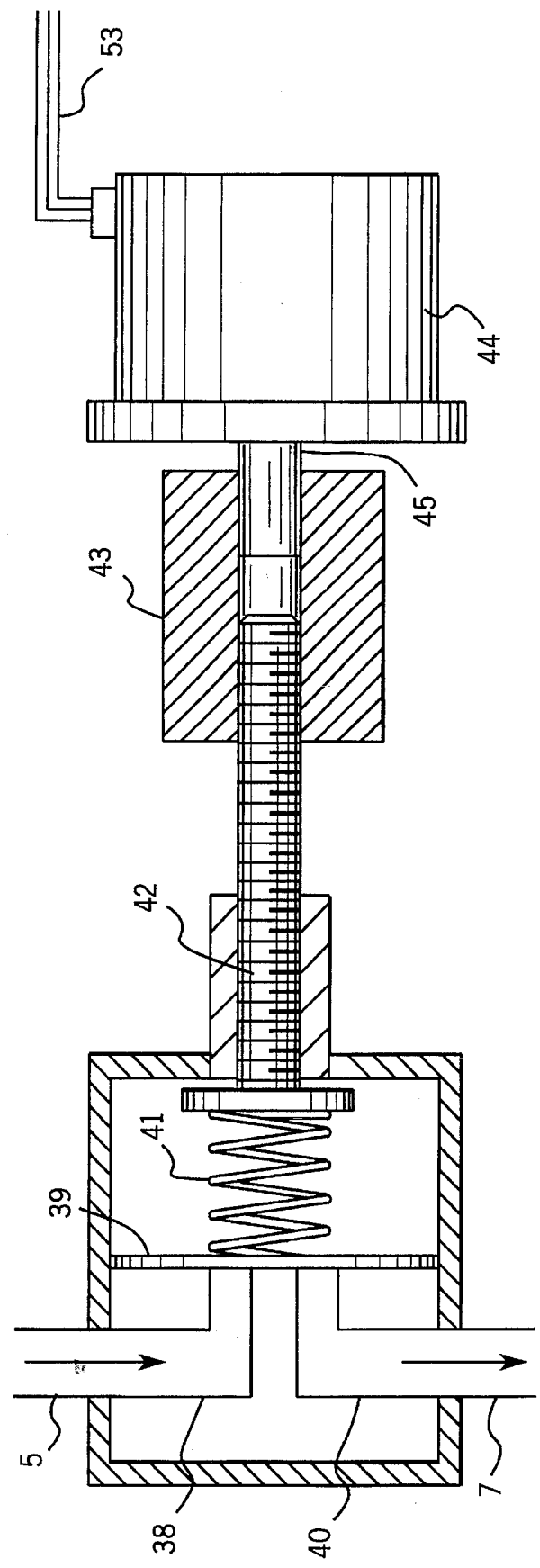
FIG. 2 is a sectional view of one possible pressure regulating element, shown in FIG. 1 and useful in an apparatus and method of the invention.

FIG. 2 illustrates one commercially available pressure regulating element 6, which is conventional but well suitable for use in a control unit as described herein. The propellant gas comes along duct 5 to a supply tube 38 for the pressure regulating element, said tube terminating in a valve disc 39. On the other hand, an outlet tube 40, carrying propellant gas away from pressure regulating element 6 and having one end thereof connected for duct 7, commences from valve disc 39. Thus, the valve disc separates the trailing or discharge end of the supply tube from the leading or inlet end of the outlet tube. The propellant gas pressure strives to push valve disc 39 backwards for allowing the propellant gas to discharge from tube 38 into tube 40. The initial pressure of a propellant gas discharging into tube 40 is adjusted by alteration of the tension of a spring 41 acting on valve disc 39 by means of the position of a set screw 42 in contact with this spring which is altered by means of a guide sleeve 43. The set screw 42 is connected to guide sleeve 43 in a manner that rotation of the guide sleeve around its center axis moves said set screw toward or away from valve disc 39 according to the guide sleeve rotating direction. Rotation of the guide sleeve is preferably effected by means of a stepping motor 44. Stepping motor 44 is connected to guide sleeve 43 by rotor shaft 45.

Figure 3:
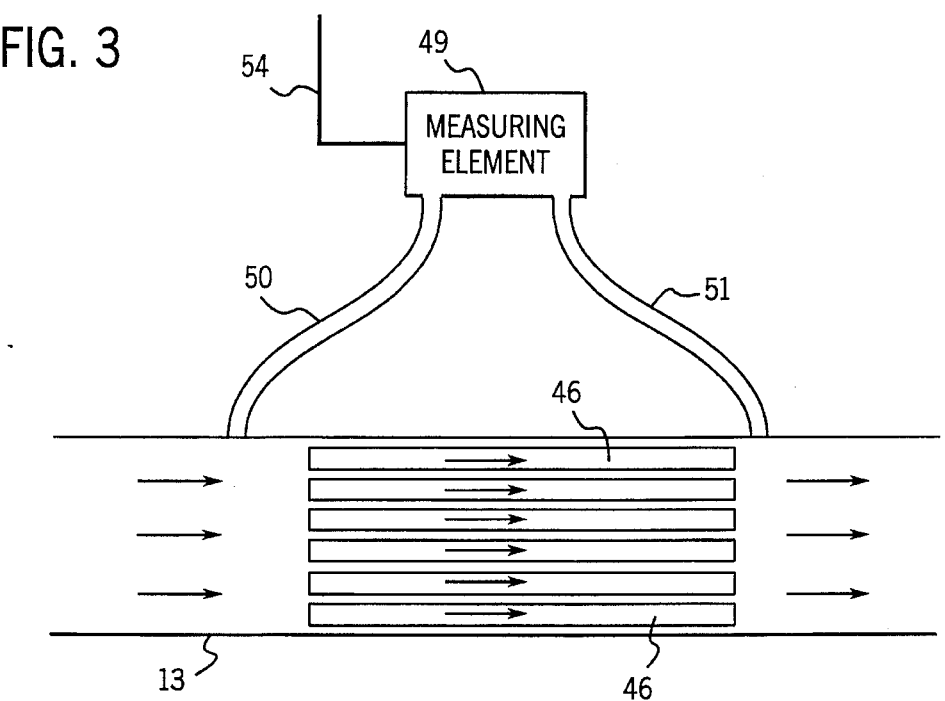
FIG. 3 shows a longitudinal section of one possible flow measuring element, shown in FIG. 1 and useful in an apparatus and method of the invention.
Figure 4:
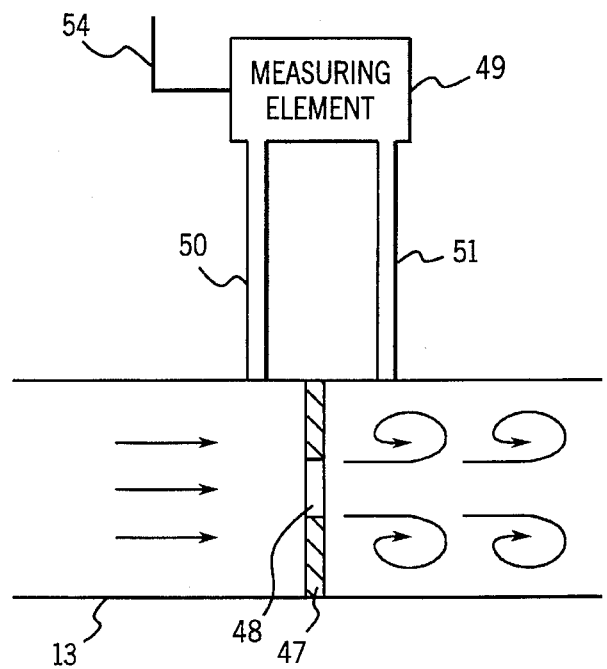
FIG. 4 shows a longitudinal section of another possible flow measuring element, shown in FIG. 1 and useful in an apparatus and method of the invention.

FIGS. 3 and 4 illustrate longitudinal sections of conventional flow measuring elements 10, which are well suitable for use in the assembly of FIG. 1. The elements shown in both figures and intended for flow measurement are pressure-difference measuring elements. The throttle is preferably maintained constant during the measurements but, if desired, the throttle can be varied according to the measuring requirements. FIG. 3 illustrates a laminar flow restricting element, which is constructed by dividing the interior of propellant gas duct 13 into a plurality of small tubes 46, each of said tubes maintaining a laminar flow within an appropriate measuring range. Thus, said tubes 46 serve as a flow restricting element or a choke.

FIG. 4 illustrates a turbulent flow restricting element, comprising a disc 47, extending around the interior of duct 13 and set against the flow and, thus, serving in this case as a choke or a throttle, and having a hole 48 in the middle for discharging the propellant gas flowing along duct 13. Another conventional solution is a reversed structure, i.e. a flow blocking disc is placed in the middle of a duct for discharging the gas between the disc and the inner wall of a duct. After finding its way around a block placed in its passage, the flow strives to carry on its passage in a turbulent form, as shown in FIG. 4.

FIGS. 3 and 4 illustrate also a measuring element 49, detecting a pressure difference and receiving signals along measuring channels 50 and 51 from both sides of the flow restricting elements.

If a pressure-difference based flow measurement is not effected, the control of a propellant gas pressure is preferably facilitated by placing a flow restricting element or a throttle 46 or 47 between pressure regulating element 6 and propellant gas chamber 18. This provides for a larger regulating range for the propellant pressure and a more accurate control of the flow rate.

The operation of a control unit appearing in a preferred solution of the invention shown in FIG. 1 as well as that of the entire ventilator is electronically controlled. The operation is controlled by a processor 52. Thereby, and along a line 53, the initial pressure of pressure regulating element 6 can be varied to match a desired propellant gas flow. In the case shown in FIG. 1, the correction or feedback is effected on the basis of a signal received from flow measuring element 10 along a line 54. A flow measurement message received from element 10, which is thus preferably an element measuring the pressure difference over a throttle, is transmitted via an amplifier 55 and an A/D-converter 56 to microprocessor 52.

Instead of, or preferably in addition to flow measuring element 10, the initial pressure of pressure regulating element 6 can be monitored by means of pressure measuring element 11. The output voltage of element 11 carried along a line 57 is amplified by amplifier 55 and converted by A/D-converter into a binary form and read by microprocessor 52.

Microprocessor 52 is used to regulate the initial pressure of pressure regulating element 6 by controlling the rotation of stepping motor 44 if the measured flow and/or pressure differs from a desired propellant gas flow rate. In this case, the processor calculates correction terms for the control of a stepping motor. The control of a stepping motor is stopped when a calibration value stored in the microprocessor memory matches a signal received from the flow measuring element or pressure measuring elements 11. The correction of the initial pressure of pressure regulating element 6 can preferably be effected during both an inhalation and exhalation cycle.

Processor 52 is preferably also used for controlling the operation of inspiration valve 8 and outlet valve 9. The opening and closing of the inspiration and outlet valves is determined by means of a preset relationship between respiration frequency and inhalation and exhalation times.

A signal from a pressure measuring element 60 included in the patient circuit is also preferably delivered to processor 52.

The invention is by no means limited to the above embodiments but various details of the invention can be modified within the scope of the appended claims. The drawing only illustrates the construction and operation of just one pressure regulating element 6. It is obvious that other types of pressure regulating elements can be used just as well within the scope of the invention. Neither is the invention by any means limited to the illustrated assembly of a patient circuit and a bellows unit. There is merely described one possible functional and conventional solution for a patient circuit and a bellows unit.

We claim:

1. Apparatus for regulating the volume of a breathing gas delivered to a patient during an inhalation phase of a respiratory cycle, said respiratory cycle also having an expiration phase, said apparatus employing propellant gas from a propellant gas source and comprising:

a propellant gas chamber;

supply conduit means extending from the propellant gas source to said propellant gas chamber for providing a flow of propellant gas from the gas source to said propellant gas chamber;

discharge conduit means for discharging propellant gas from said propellant gas chamber;

a second gas chamber containing breathing gas and separated by a wall from said propellant gas chamber, said wall being movable responsive to the pressure of the propellant gas in said propellant gas chamber for altering the volume of said second gas chamber, said second gas chamber delivering breathing gas to the patient in the inhalation phase and receiving gas expired by the patient in the expiration phase as a result of the supply and discharge of propellant gas to and from the propellant gas chamber;

a controllable pressure regulator interposed in said supply conduit means and having an input connected to the propellant gas source and an output coupled to said propellant gas chamber for discharging gas at a pressure determined by the pressure regulating action of said controllable pressure regulator;

means interposed in said supply conduit means, said means sensing and responding to the flow of propellant gas through said supply conduit means for measuring a selected physical property of the flowing propellant gas indicative of the amount of gas delivered to said propellant gas chamber; and control means coupled to said controllable pressure regulator and said measuring means for operating said controllable pressure regulator responsive to the measurement of said selected physical property to regulate propellant gas pressure to establish a desired propellant gas flow magnitude to the propellant gas chamber during the inhalation phase.

2. Apparatus as set forth in claim 1 further including pressure measuring means interposed in said supply conduit means downstream of said controllable pressure regulator in the flow direction of the propellant gas, said pressure measuring means being coupled to said control means for said controllable pressure regulator.

3. Apparatus as set forth in claim 1 wherein said discharge conduit means includes valve means for discharging propellant gas from said propellant gas chamber.

4. Apparatus as set forth in claim 1, wherein said controllable pressure regulator is further defined as means for permitting or shutting off the flow of propellant gas from the gas source to said propellant gas chamber.

5. Apparatus as set forth in claim 4 wherein said controllable pressure regulator comprises a pressure relief valve.

6. Apparatus as set forth in claim 4 wherein said controllable pressure regulator is further defined as a motor operated pressure regulator.

7. Apparatus as set forth in claim 1 wherein said supply conduit means further includes a valve for controlling the flow of propellant gas from the gas source to said propellant gas chamber.

8. Apparatus as set forth in claim 7 wherein said supply conduit means includes further valve means for discharging propellant gas from said propellant gas chamber.

9. Apparatus according to claim 7 wherein said valve is interposed between said controllable pressure regulator and said propellant gas chamber.

10. Apparatus according to claim 1 wherein said measuring means comprises gas flow measuring means.

11. Apparatus according to claim 10 wherein said gas flow measuring means is interposed between said controllable pressure regulator and said propellant gas chamber.

12. Apparatus as set forth in claim 10 wherein said gas flow measuring means includes pressure-difference measuring means.

13. Apparatus as set forth in claim 10 further including pressure measuring means interposed in said supply conduit means downstream of said controllable pressure regulator in the flow direction of the propellant gas, said pressure measuring means being coupled to said control means for said controllable pressure regulator.

14. A method for regulating the volume of a breathing gas delivered to a patient during an inhalation phase of a respiratory cycle, said method comprising the steps of:

providing a flow of propellant gas from a propellant gas source to a propellant gas chamber during the inhalation phase for delivering breathing gas to the patient from a second gas chamber separated from the propellant gas chamber by a wall that is movable responsive to the supply of propellant gas to the propellant gas chamber;

sensing the flow of propellant gas to the propellant gas chamber;

measuring a selected physical property of the flowing propellant gas as a result of the sensing; and regulating the pressure of the propellant gas provided to the propellant gas chamber in accordance with the measurement of the selected physical gas property to establish a desired propellant gas flow magnitude to the propellant gas chamber during the inhalation phase.

15. A method as set forth in claim 14 wherein the sensing and measuring steps are further defined as sensing and measuring the pressure of the propellant gas downstream, in the flow direction of the propellant gas, from a point at which the pressure of the propellant gas is regulated.

16. A method as set forth in claim 14 wherein the respiratory cycle of the patient also includes an exhalation phase and wherein the method is further defined as including the step of discharging propellant gas from the propellant gas chamber during the exhalation phase.

17. A method as set forth in claim 14 wherein the sensing and measuring steps are further defined as sensing and measuring the flow magnitude of the propellant gas.

18. A method as set forth in claim 17 wherein the sensing and measuring steps are further defined as sensing and measuring the pressure of the propellant gas downstream, in the flow direction of the propellant gas, from a point at which the pressure of the propellant gas is regulated.

* * * * *